United States Patent [19]

Hirayama et al.

[11] 4,234,450

[45] Nov. 18, 1980

[54] PREPARATION OF NON-FLUIDIZABLE COMPOSITION

[75] Inventors: Masami Hirayama; Tadataka Nakata; Michiko Kagayama, all of Nara, Japan

[73] Assignee: Rohto Pharmaceutical Co. Ltd., Japan

[21] Appl. No.: 884,992

[22] Filed: Mar. 9, 1978

[30] Foreign Application Priority Data

Mar. 12, 1977 [JP] Japan .................................. 52/27213

[51] Int. Cl.³ .............................................. B01J 13/00
[52] U.S. Cl. .................................... 252/314; 252/312;
252/316; 424/73; 424/DIG. 5
[58] Field of Search ........................ 252/312, 314, 316;
424/73, DIG. 5

[56] References Cited

U.S. PATENT DOCUMENTS

| | | |
|---|---|---|
| 3,154,470 | 10/1964 | Braun et al. .................... 424/DIG. 5 |
| 3,259,545 | 7/1966 | Teller ............................. 424/DIG. 5 |
| 3,296,076 | 1/1967 | Thomä ................................... 424/73 |
| 3,507,806 | 4/1970 | Barker et al. ..................... 252/312 X |
| 4,017,641 | 4/1977 | DiGiulio ............................ 424/73 X |
| 4,062,937 | 12/1977 | Rea ................................. 424/DIG. 5 |

*Primary Examiner*—Richard D. Lovering
*Attorney, Agent, or Firm*—Craig & Antonelli

[57] ABSTRACT

A non-fluidizable composition readily convertible into a fluidizable composition by slight stress or pressure, which can be prepared by cooling an emulsion comprisinng a water-immiscible fatty acid, water and an emulsifier from a temperature sufficient to keep the emulsion at a fluidizable state while stirring, stopping the stirring at a temperature not lower than the temperature 5° C. below the congealing temperature of the emulsion and further continuing the cooling to room temmperature and is useful as a base for shaving creams, hair creams, adhesive pastes, printers' inks, shoe polishes, etc.

15 Claims, 8 Drawing Figures

PREPARATION OF NON-FLUIDIZABLE COMPOSITION

The present invention relates to a non-fluidizable composition and its preparation. More particularly, it relates to a non-fluidizable composition formed in a certain shape, which is readily convertible into a fluidizable composition by stress or pressure, and its preparation.

Conventional creamy compositions useful as cosmetics, shoe polishes, etc. do not have any fixed shape and are usually accommodated in appropriate containers, from which they are taken out by the user with a finger or a spatula and applied to the surface of an object. However, such use manner is not only troublesome but also unsanitary.

It has now been found that a non-fluidizable composition obtained by cooling an emulsion comprising a water-immiscible fatty acid, water and an emulsifier from a temperature sufficient to keep the emulsion at a fluidizable state to room temperature through the congealing temperature of the emulsion in a certain special manner can be readily converted into a composition fluidizable by slight stress or pressure. Different from the so-called "thixotropy" under which a composition once liquefied and made fluidizable resumes its original non-fluidizable form after removal of stress or pressure applied thereto, the above mentioned composition does not resume its non-fluidity after once made fluidizable. This phenomenon is advantageously utilizable for preparation of a composition which is to be kept in a non-fluidizable state prior to its application and in a fluidizable state on and after its application. Typical examples of such composition are shaving creams, hair creams, adhesive pastes, printers' inks, shoe polishes, etc.

Accordingly, a basic object of the present invention is to provide a non-fluidizable composition which can be readily made fluidizable by slight stress or pressure. Another object of this invention is to provide a base composition for cosmetics, pharmaceuticals, adhesives, etc. which is non-fluidizable but easily made fluidizable by slight stress or pressure. A further object of the invention is to provide a process for preparation of a non-fluidizable composition which can be made fluidizable by slight stress or pressure. These and other objects will be apparent to those skilled in the art from the foregoing and subsequent descriptions.

The non-fluidizable composition of the present invention can be prepared by allowing an emulsion comprising a water-immiscible fatty acid, water and an emulsifier to cool from a temperature sufficient to keep the emulsion at a fluidizable state while stirring, stopping the stirring at a temperature not lower than the temperature 5° C. below the congealing temperature of the emulsion and further continuing the cooling to room temperature. When the initial cooling (i.e. cooling while stirring) is finished, the emulsion may be charged in a container of appropriate form to be submitted for the practical use, followed by subsequent cooling (i.e. cooling without stirring) so that a non-fluidizable composition is formed in the container. The thus prepared non-fluidizable composition can be readily liquefied by slight stress or pressure to make a fluidizable composition.

The present invention will be hereinafter illustrated in the accompanying drawings and described more in details taking a shaving cream composition in a stick form as an example, wherein.

Figure 4:
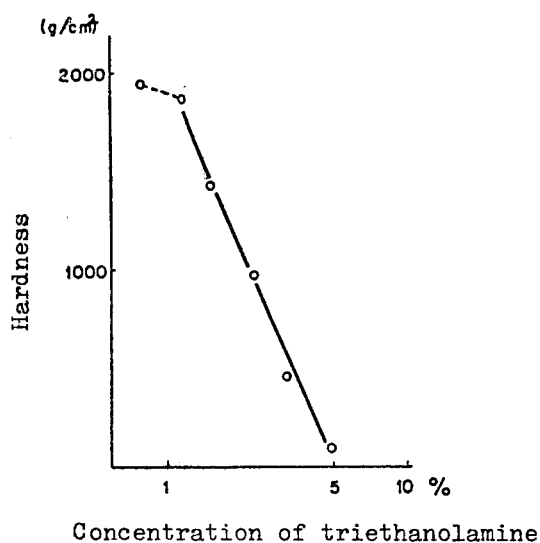
Figure 5:
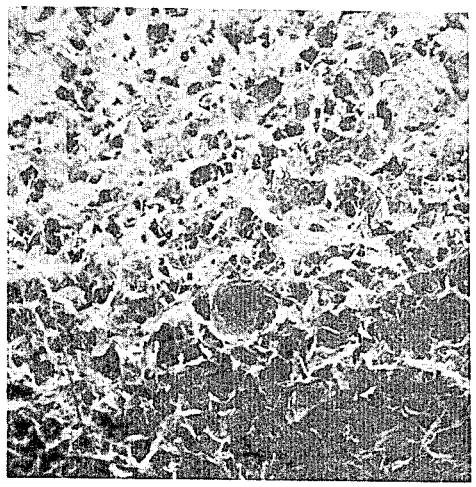
Figure 6:
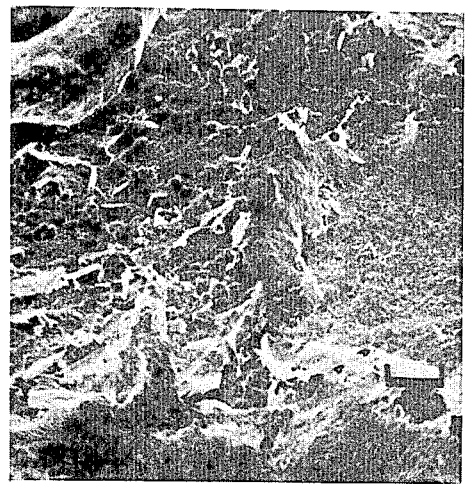
Figure 7:
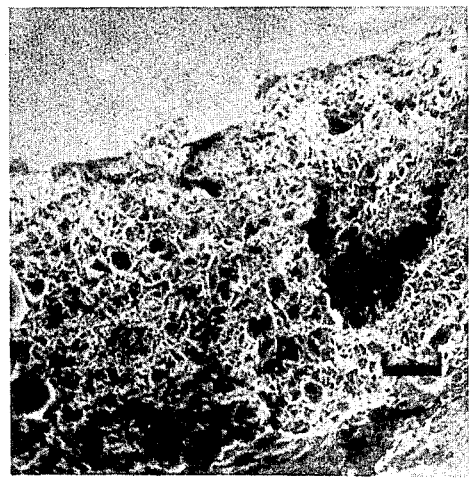
Figure 8:
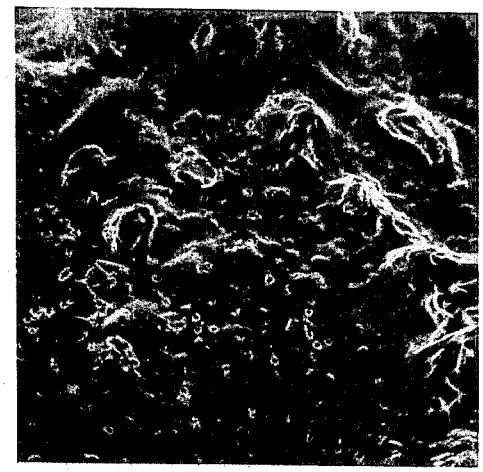

FIG. 4 is a graphical representation showing the relationship between the hardness of the composition of the invention and the concentration of triethanolamine before application; and FIGS. 5 through 8 are microphotographs of fluidizable compositions, FIGS. 5 and 7 being prepared by the process of this invention respectively with myristic acid and palmitic acid and FIGS. 6 and 8 being prepared by another procedure with cooling to room temperature respectively with myristic and palmitic acid.

For preparation of a shaving cream composition in a stick form according to the present invention, an oily composition comprising a water-immiscible saturated fatty acid and an aqueous composition comprising water, at least one of the compositions containing an emulsifier, are mixed together at a temperature sufficient to keep the resulting mixture at a fluidizable state (usually from about 50° to 80° C.). The resulting mixture forms an oil-in-water emulsion, which is allowed to cool while stirring. At a temperature not lower than the temperature 5° C. below the congealing temperature of the emulsion, usually between about 40° and 60° C., the stirring is stopped. The difference between the temperature sufficient to keep the mixture at a fluidizable state and the congealing temperature is not critical but the former is preferably set at a temperature 10° to 15° C. higher than the latter. Then, the emulsion is charged in a container of cylindrical form, and the cooling is continued to room temperature, whereby a non-fluidizable composition in a stick form is obtained.

The congealing temperature is defined as the temperature at which a substance passes from the liquid to the solid state upon cooling (cf. United States Pharmacopeia XIX, 642, 1975) and determined by the method of Japanese Pharmacopeia IX, B-47, 1976.

Figure 1:
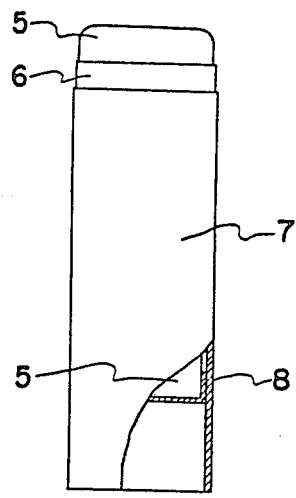
FIG. 1 is a front view, partially in section, of a container for the composition of the invention in stick form.

As the container, there may be used any one conventionally employed for solid hair dressing agents in a stick form. A typical example is shown in FIG. 1 of the accompanying drawings, which is a front view with a partial section view of such container. In this Figure, a shaving cream composition in a stick form (5) is retained on a cylindrical retainer (8) and slidably inserted in a cylindrical body (7) having open ends at both terminals. On the use, the bottom of the retainer (8) is pushed by a finger so that the tip of the stick body (5) projects over the neck portion (6) of the cylindrical body (7), and the projected tip is rubbed onto a skin with slight pressure, whereby a fluidizable creamy composition is applied onto the skin.

Examples of the water-immiscible saturated fatty acid are those having 12 to 18 carbon atoms such as lauric acid, myristic acid, palmitic acid or stearic acid. These fatty acids may be used alone or in combination. The concentration of the fatty acid in the emulsion may be usually from about 10 to 50% by weight based on the weight of the emulsion. In general, a higher concentration of the fatty acid affords a non-fluidizable composition having an increased hardness.

At the emulsifier, there are ordinarily employed non-ionic surfactants such as polyoxyethylene sorbitan monostearate, polyoxyethylene sorbitan monooleate, polyoxyethylene stearate, polyoxyethylene cetyl alcohol ether and polyoxyethylene nonylphenyl ether. Solubilizing aids such as hydroxy group-containing amines (e.g. triethanolamine, diethanolamine) or alkali hydroxides (e.g. sodium hydroxide, potassium hydroxide) may be also employed as the emulsifier. These emusifiers can be used alone or in combination. The concentration of the emulsifier is varied with the kind of the emulsifier, the kind of the fatty acid, the amount of the fatty acid, etc. and normally it may be from about 1 to 5% by weight based on the weight of the emulsion. Particularly when the said solubilizing aid is employed, its concentration in the emulsion is preferred to be from about 1.2 to 3.2% by weight.

In addition to the said essential components, the emulsion may optionally include any additive. Examples of such additive are waxes (e.g. spermaceti, hydrous lanolin), hydrocarbons (e.g. liquid paraffin, paraffin wax), esters (e.g. isopropyl myristate), polyols (e.g. glycerol, propylene glycol, polyethylene glycol), carboxymethyl cellulose sodium, etc. The concentration of these additives in the emulsion is usually not more than about 20% by weight.

Further, small amounts of cosmetically effective components, refreshing agents, perfumes, antiseptics, etc. may be incorporated into the emulsion.

The amount of water in the emulsion is usually within a range of 60 to 80% by weight of the emulsion.

The temperature at which the initial cooling with stirring is finished and the subsequent cooling without stirring is initiated affords a great influence on the hardness of the resultant non-fluidizable composition. Both of the initial cooling and the subsequent cooling may be effected, for instance, by exposing the emulsion to ambient conditions or by contacting the emulsion with a coolant. The optimum temperature is more or less associated with the kind of the fatty acid, but it is usually about 5° C. higher than the congealing temperature of the starting emulsion.

The thus prepared shaving cream composition in a stick form according to the invention has a hardness close to that of conventional solid hair dressing agents before application and is readily made fluidizable by slight stress or pressure on its application. The hardness after application is nearly equal to that of conventional shaving creams. Therefore, the composition can be applied onto a skin directly from a container accommodating the same and, after the application, used in the entirely same manner as a conventional shaving cream composition.

The present invention will be illustrated in further details by the following Examples and Tests, wherein percentage(s) (%) and part(s) are by weight. The abbreviations "POE" and "CMC-Na" indicate respectively "polyoxyethylene" and "carboxymethyl cellulose sodium".

EXAMPLE 1

An oily mixture comprising myristic acid (22.0%), liquid paraffin (light, 4.0%), isopropylmethylphenol (0.3%), diphenhydramine (0.2%), perfumes (0.7%), and POE (20) sorbitan monostearate (2.5%) and an aqueous mixture comprising Macrogol 400 (3.0%), propylene glycol (1.0%), CMC-Na (0.3%), triethanolamine (1.6%), glycerol (8.0%) and water (56.4%) were mixed together and stirred at about 75° C. to make an emulsion. The emulsion was allowed to cool to 60° C. while stirring, filled into a container and then allowed to cool to room temperature, whereby a non-fluidizable shaving cream composition accommodated in the container was obtained. The composition had a hardness of 1427 g/cm$^2$ (measured as in Test 1), and when applied to a skin, it turned into a fluidizable creamy form.

EXAMPLES 2 TO 5

The components and physical properties of some non-fluidizable shaving cream compositions prepared in the same manner as in Example 1 are shown in Table 1.

TABLE 1

| Product | | | Example 2 | 3 | 4 | 5 |
|---|---|---|---|---|---|---|
| Composition (%) | Oily mixture | Myristic acid | 22.0 | 22.0 | 22.0 | 22.0 |
| | | Paraffin wax | 5.0 | | | |
| | | Spermaceti | | 5.0 | | |
| | | Isopropyl myristate | | | 5.0 | |
| | | Refined hydrous lanolin | | | | 5.0 |
| | | POE (20) sorbitan monostearate | 2.5 | 2.5 | 2.5 | 2.5 |
| | Aqueous mixture | CMC-Na | 0.3 | 0.3 | 0.3 | 0.3 |
| | | Triethanolamine | 1.2 | 1.2 | 1.2 | 1.2 |
| | | Water | 69.0 | 69.0 | 69.0 | 69.0 |
| Hardness before application (g/cm$^2$) | | | 1141 | 953 | 887 | 1239 |
| State after application | | | Soft cream | Soft cream | Soft cream | Soft cream |
| Temperature at which stirring was stopped (°C.) | | | 60 | 60 | 60 | 60 |

EXAMPLES 6 TO 9

The components and physical properties of some non-fluidizable shaving cream compositions prepared in the same manner as in Example 1 are shown in Table 2.

TABLE 2

| Product | | | Example 6 | 7 | 8 | 9 |
|---|---|---|---|---|---|---|
| Composition (%) | Oily mixture | Lauric acid | 25.0 | | | |
| | | Myristic acid | | 22.0 | | |
| | | Palmitic acid | | | 30.0 | |
| | | Stearic acid | | | | 30.0 |
| | | Liquid Paraffin (light) | 4.0 | 4.0 | 4.0 | 4.0 |
| | | POE (20) sorbitan monostearate | 2.5 | 2.5 | 2.5 | 2.5 |
| | Aqueous mixture | Triethanolamine | 1.2 | 1.2 | 1.2 | 1.2 |
| | | CMC-Na | 0.3 | 0.3 | 0.3 | 0.3 |
| | | Purified water | 67.0 | 70.0 | 62.0 | 62.0 |
| Hardness before application (g/cm$^2$) | | | 1045 | 1141 | 1566 | 1375 |
| Hardness after application (g/cm$^2$) | | | 5.8 | 2.8 | 1.0 | 1.6 |
| Temperature at which stirring was stopped (°C.) | | | 60 | 60 | 60 | 60 |

EXAMPLES 10 TO 13

The components and physical properties of some non-fluidizable shaving cream compositions prepared in the same manner as in Example 1 are shown in Table 3.

TABLE 3

| | | Product | Example 10 | Example 11 | Example 12 | Example 13 |
|---|---|---|---|---|---|---|
| Composition (%) | Oily mixture | Myristic acid | 22.0 | | 22.0 | 22.0 |
| | | Palmitic acid | | 22.0 | | |
| | | Liquid paraffin (light) | 4.0 | 4.0 | 4.0 | 4.0 |
| | | POE (20) sorbitan monostearate | | 3.0 | 2.5 | 2.5 |
| | Aqueous mixture | Triethanolamine | 1.2 | | | |
| | | NaOH | | | 0.4 | |
| | | KOH | | | | 0.5 |
| | | CMC-Na | 0.3 | 0.3 | 0.3 | 0.3 |
| | | Purified water | 72.5 | 70.7 | 70.8 | 70.7 |
| Hardness before application (g/cm$^2$) | | | 694 | 4824 | 2143 | 1681 |
| State after application | | | Soft cream | Soft cream | Soft cream | Soft cream |
| Temperature at which stirring was stopped (°C.) | | | 60 | 50 | 60 | 60 |

EXAMPLES 14 TO 17

The components and physical properties of some non-fluidizable shaving cream compositions prepared in the same manner as in Example 1 are shown in Table 4.

TABLE 4

| | | Product | Example 14 | Example 15 | Example 16 | Example 17 |
|---|---|---|---|---|---|---|
| Composition (%) | Oily mixture | Myristic acid | 22.0 | 22.0 | 22.0 | 22.0 |
| | | Liquid paraffin | 4.0 | 4.0 | 4.0 | 4.0 |
| | | POE (25) stearate | 8.8 | | | |
| | | POE (30) cetyl alcohol ether | | 8.8 | | |
| | | POE (20) sorbitan monooleate | | | 8.8 | |
| | | POE (20) nonyl phenyl ether | | | | 8.8 |
| | Aqueous mixture | Triethanolamine | 1.2 | 1.2 | 1.2 | 1.2 |
| | | CMC-Na | 0.3 | 0.3 | 0.3 | 0.3 |
| | | Purified water | 63.7 | 63.7 | 63.7 | 63.7 |
| Hardness before application (g/cm$^2$) | | | 1418 | 1169 | 1455 | 1723 |
| State after application | | | Soft cream | Soft cream | Soft cream | Soft cream |
| Temperature at which stirring was stopped (°C.) | | | 60 | 60 | 60 | 60 |

TEST 1

Hardness was determined on the shaving cream composition in a stick form prepared in Example 1 and conventional creamy cosmetics. A metal plate having a diameter of 3 or 15 mm was inserted into a specimen charged in a container from the upper surface at a rate of 20 mm per minute, and a maximum resistance (g/cm$^2$) when inserted up to 10 mm in depth was measured by the use of a reometer (manufactured by Fudo Kogyo K.K.). Hardness after the application indicates the value measured on a specimen which was liquefied by pressing slightly the specimen onto a cooking foil and drawing a round of 60 mm in diameter at a rate of 100 rotations per minute. The results are shown in Table 5.

TABLE 5

| Specimen | Use | Hardness (g/cm$^2$) | |
|---|---|---|---|
| Commercial product A | Shaving cream | 4.3 | |
| Commercial product B | Shaving cream | 3.1 | |
| Commercial product C | Skin cream | 40 | |
| Commercial product D | Skin cream | 15 | |
| Commercial product E | Solid hair dressing agent | 7268 | |
| Commercial product F | Solid hair dressing agent | 6169 | |
| Present invention (Example 1) | Shaving cream | 1141 | (before appln.) |
| | | 2.8 | (after appln.) |

As understood from the above table, the shaving cream composition of the invention has a hardness close to that of conventional solid hair dressing agents before application and shows a hardness close to that of conventional shaving creams after application.

TEST 2

The hardness of a shaving cream composition comprising the following components was measured in the same manner as described in Test 1:

| Components | Part(s) by weight |
|---|---|
| Fatty acid | Appropriate amount |
| Liquid paraffin | 4 |
| Polysorbate 60 | 2.5 |
| Triethanolamine | 1.2 |
| Carboxymethyl cellulose sodium | 0.3 |
| Water | To make 100 |

Figure 2:
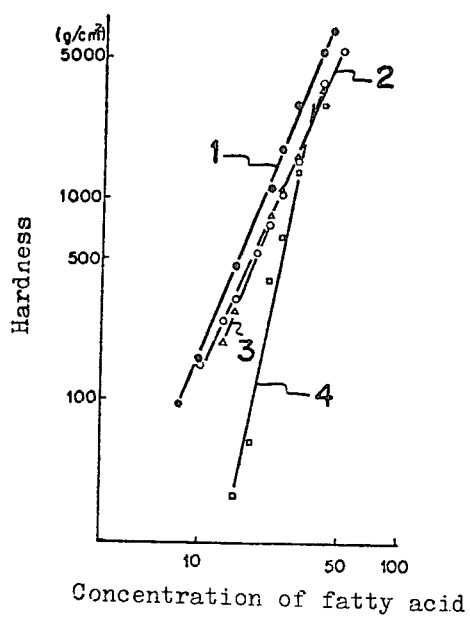
FIGS. 2 and 3 are graphical representations, respectively, illustrating the relationship between the hardness and the concentration of fatty acid in the composition of the invention before and after application.

The results are shown in FIGS. 2 (before application) and 3 (after application) of the accompanying drawings, wherein the axis of abscissa and the axis of ordinate indicate respectively the concentration of the fatty acid (% by weight) and the hardness (g/cm$^2$) and the lines (1), (2), (3) and (4) correspond respectively to the cases using as the fatty acid, myristic acid, lauric acid, palmitic acid and stearic acid.

Figure 3:
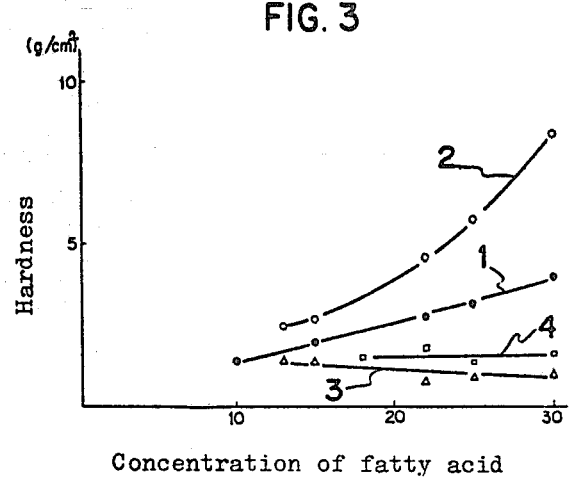

As understood from FIGS. 2 and 3, the hardness of the shaving cream composition before application increases with the elevation of the concentration of the fatty acid irrespective of the kind of the fatty acid, and the hardness after application is not remarkably influenced by the kind and/or concentration of the fatty acid.

TEST 3

The hardness of a shaving cream composition comprising the following components was measured in the same manner as described in Test 1:

| Components | Part(s) by weight |
|---|---|
| Myristic acid | 30 |
| Liquid paraffin | 4 |
| Polysorbate 60 | 2.5 |
| Triethanolamine | Appropriate amount |
| Carboxymethyl cellulose sodium | 0.3 |
| Water | To make 100 |

The results are shown in FIG. 4 (before application) wherein the axis of abscissa and the axis of ordinate indicate respectively the concentration of triethanolamine (% by weight) and the hardness (g/cm$^2$).

From this Figure, it is understood that the use of triethanolamine in an excessive amount can not provide the shaving cream composition with a satisfactory hardness.

TEST 4

A fatty acid (22 parts), liquid paraffin (4 parts) and polysorbate 60 (2.5 parts) were mixed together to make an oil mixture, and separately carboxymethyl cellulose sodium (0.3 part), triethanolamine (1.2 parts) and water (70 parts) were mixed together to make an aqueous mixture. These mixtures were combined together while stirring at about 80° C. to make an emulsion. The emulsion was allowed to cool to a certain temperature under stirring and then to room temperature without stirring to give a non-fluidizable composition, of which the hardness was determined in the same manner as in Test 1.

The results are shown in Table 6, from which it may be understood that the stoppage of stirring at a certain temperature which is varied with the kind of the fatty acid is necessary to obtain an appropriate hardness.

TABLE 6

| Temperature at which stirring was stopped (°C.) | Hardness (g/cm$^2$) | | | |
|---|---|---|---|---|
| | Lauric acid | Myristic acid | Palmitic acid | Stearic acid |
| 60 | 745 | 1141 | 828 | 395 |
| 55 | — | — | — | 225 |
| 50 | 864 | 1186 | 743 | 26 |
| 45 | — | — | 592 | 12 | — |
| 40 | 888 | 10 | 6 | 18 |
| 35 | 24 | — | — | — |
| Congealing temperature (°C.) | 37.6 | 48.1 | 54.2 | 59.9 |

TEST 5

A fatty acid (22 parts), liquid paraffin (4 parts) and polysorbate 60 (2.5 parts) were mixed together, and separately carboxymethyl cellulose sodium (0.3 part), triethanolamine (1.2 parts) and water (70 parts) were mixed together. These mixtures were combined together at about 80° C. while stirring to make an emulsion. The emulsion was allowed (A) to cool to room temperature while stirring, or (B) to cool to a temperature about 5° C. higher than the congealing temperature of the emulsion while stirring and then to room temperature without stirring, whereby a non-fluidizable composition was obtained.

The thus obtained fluidizable composition was microscopically observed, and the results are shown in FIGS. 5 to 8 which correspond respectively to the microscopic photographs (×30 folds) of the compositions prepared by the use of myristic acid according to the procedure (B), by the use of myristic acid according to the procedure (A), by the use of palmitic acid according to the procedure (B) and by the use of palmitic acid according to the procedure (A). From these Figures, it is understood that the compositions according to the procedure (B) have a net-like structure (cf. FIGS. 5 and 7) and the compositions according to the procedure (A) do not have such structure (cf. FIGS. 6 and 8).

What is claimed is:

1. A process for preparing a non-fluidizable composition readily convertible into a fluidizable composition by slight stress or pressure, which comprises the steps of cooling an emulsion consisting essentially of a water-immiscible saturated fatty acid, water within a range of from 60–80% by weight of the emulsion, and an emulsifier selected from the group consisting of a non-ionic surfactant, a solubilizing aid and a mixture thereof, said solubilizing aid being selected from the group consisting of a hydroxy group-containing amine and an alkali hydroxide from a temperature sufficient to keep the emulsion in a fluidizable state while stirring, stopping the stirring at a temperature not lower than the temperature 50° C. below the congealing temperature of the emulsion and continuing further the cooling to room temperature.

2. The process according to claim 1, wherein the concentration of the saturated fatty acid in the emulsion is from about 10 to 50% by weight.

3. The process according to claim 2, wherein the concentration of the emulsifier in the emulsion is from about 1 to 5% by weight.

4. The process according to claim 2, wherein the concentration of the emulsifier in the emulsion is from about 1.2–3.2% by weight.

5. The process according to claim 1, wherein the saturated fatty acid is a saturated fatty acid having 12 to 18 carbon atoms.

6. The process according to claim 5, wherein the saturated fatty acid is a member selected from the group consisting of lauric acid, myristic acid, palmitic acid and stearic acid.

7. The process according to claim 1, wherein the non-ionic surfactant is a member selected from the group consisting of polyoxyethylene sorbitan monostearate, polyoxyethylene sorbitan monooleate, polyoxyethylene stearate, polyoxyethylene cetyl alcohol ether and polyoxyethylene nonylphenyl ether.

8. The process according to claim 1, wherein the solubilizing aid is ethanolamine.

9. The process according to claim 1, wherein the emulsifier is a mixture of the non-ionic surfactant and ethanolamine.

10. The process according to claim 1, wherein the temperature from which the initial cooling with stirring is started is from about 50° to 80° C.

11. The process according to claim 1, wherein the temperature from which the subsequent cooling without stirring is started is from about 40° to 60° C.

12. The process according to claim 1, wherein the emulsion to be cooled is charged in a container.

13. The process according to claim 1, wherein the emulsion after the initial cooling and before the subsequent cooling is charged in a container.

14. The process according to claim 13, wherein the container has a cylindrical form suitable for making the non-fluidizable composition in a stick form.

15. The process according to claim 1, further comprising initially forming said emulsion from said fatty acid, water and said emulsifier at a temperature of from 50°–80° C.

* * * * *